(12) United States Patent
Veis et al.

(10) Patent No.: US 7,528,940 B2
(45) Date of Patent: May 5, 2009

(54) SYSTEM AND METHOD FOR INSPECTING AN OBJECT USING AN ACOUSTO-OPTIC DEVICE

(75) Inventors: Alexander Veis, Kadima (IL); Yoram Saban, Shoham (IL)

(73) Assignee: Applied Materials, Israel, Ltd., Rehovot (IL)

( * ) Notice: Subject to any disclaimer, the term of this patent is extended or adjusted under 35 U.S.C. 154(b) by 77 days.

(21) Appl. No.: 11/554,513

(22) Filed: Oct. 30, 2006

(65) Prior Publication Data

US 2008/0100830 A1   May 1, 2008

(51) Int. Cl.
  *G01N 21/00*   (2006.01)
(52) U.S. Cl. .............. 356/237.1; 356/237.2; 356/237.6; 359/298; 359/299; 359/305
(58) Field of Classification Search ... 356/237.1–237.6; 359/298, 299, 305, 310
  See application file for complete search history.

(56) References Cited

U.S. PATENT DOCUMENTS 6,809,808 B2 * 10/2004 Feldman et al. .......... 356/237.1
7,092,000 B2 * 8/2006 Katzir et al. ................. 347/255
2003/0137659 A1 * 7/2003 Milshtein .................. 356/237.2

* cited by examiner

*Primary Examiner*—L. G Lauchman
*Assistant Examiner*—Iyabo S Alli
(74) *Attorney, Agent, or Firm*—Tarek N. Fahmi

(57) ABSTRACT

A system and method for inspecting an object. The system includes: a traveling lens acousto-optic device adapted to generate a traveling lens that propagates through an active region of the traveling lens acousto-optic device; a first scanner, adapted to direct a beam of light towards the traveling lens while the traveling lens propagates; a first beam splitter, adapted to receive a beam formed by the traveling lens; and to split the scanned beam to multiple illuminating light beams; multiple detectors; and an objective lens; adapted to receive the multiple illuminating light beams, direct the multiple illuminating light beams towards multiple areas of the object, receive multiple collected light beams from the multiple areas of the object, and direct the multiple collected light beams towards the multiple detectors; wherein each detector is associated with an area of the multiple areas.

20 Claims, 4 Drawing Sheets

SYSTEM AND METHOD FOR INSPECTING AN OBJECT USING AN ACOUSTO-OPTIC DEVICE

FIELD OF THE INVENTION

The present invention relates to wafer defect detection systems which use a scanning laser beam to illuminate a wafer under analysis and identify defects by analysis of reflected light or transmitted light. In particular, the present invention concerns a scanner system using multiple beams that concurrently illuminate an object such as a wafer, a reticle, a mask and the like, under inspection and generate multiple corresponding reflected or transmitted beams that are concurrently detected.

BACKGROUND

A variety of systems are used for automated inspection of semiconductor wafers, in order to detect defects, particles and/or patterns on the wafer surface as part of a quality assurance process in semiconductor manufacturing processes. It is a goal of current inspection systems to have high resolution and high contrast imaging in order to provide the reliability and accuracy demanded in sub-micron semiconductor manufacturing processes. However, it is also important to have a high-speed process that permits a large volume throughput so that the quality and assurance processes do not become a bottleneck in the wafer production process. Accordingly, the optical inspection systems must use shorter wave lengths, higher numerical aperture optics and high density image capture technology in order to enable the processing of data from such systems at sufficiently high rates that will satisfy the desired product throughput requirements.

A conventional imaging architecture that is used in wafer inspection systems at this time utilizes a single spot scanning laser for high-speed imaging. However, the data rates achievable by such architectures are limited by the physical constraints that arise due to limitations in the speed and quality of the single laser beam, the applicable optical system and related detection devices. For example, the single laser acting as a point light source is focused as a spot onto the object under inspection and is scanned across the surface of the object, which may be stationary or moved on a stage mechanism in coordination with the scan. The reflected light from the object is then imaged onto a detector, which generates pixel data from the scanning process. The detector may be a photo multiplier detector (PMT) or a CCD array, whose individual elements are positioned to receive the reflected light as the beam is scanned and be read our serially, in a conventional fashion. While a high resolution may be obtained from such point source illumination, the requirement to scan each point in the field in order to construct a viewable image subjects the system to a limitation on its throughput.

The scanning of the single laser beam may be accomplished by a rotating mirror system, as seen in U.S. Pat. No. 5,065,008 or an acousto-optic cell. However, these single spot scanning architecture necessarily have a limited speed and are possibly subject to scan aberrations, low illumination brightness and potential thermal damage to the object when high brightness laser sources are used. The high data rates required to inspect the submicron structures of current semiconductor products cannot be achieved, even when a stage-type scanning system is used that moves the object relative to a fixed illumination and image location while a synchronized scanning pattern is produced by moving the single point of light over an area at the fixed location.

Accordingly, there is a need for an object scanning system that will improve object throughput, while maintaining or even improving the reliability and accuracy of the data collected during the scan of an object, whether in a stationary or stage-type system.

SUMMARY OF THE INVENTION

A system for inspecting a object, the system includes: a traveling lens acousto-optic device adapted to generate a traveling lens that propagates through an active region of the traveling lens acousto-optic device; a first scanner, adapted to direct a beam of light towards the traveling lens while the traveling lens propagates; a first beam splitter, adapted to receive a beam formed by the traveling lens; and to split the scanned beam to multiple illuminating light beams; multiple detectors; an objective lens; adapted to receive the multiple illuminating light beams, direct the multiple illuminating light beams towards multiple areas of the object, receive multiple collected light beams from the multiple areas of the object, and direct the multiple collected light beams towards the multiple detectors; wherein each detector is associated with an area of the multiple areas.

Conveniently, the first scanner is adapted to direct the beam of light towards the traveling lens such that most of the beam of light impinges on the traveling lens.

Conveniently, the beam of light scans the traveling lens acousto-optic device at during a short scanning period that is shorter than one micro-second.

The system according to claim 1 adapted to scan the multiple illuminating light beams, along a scan direction that is traverse to a direction of a mechanical movement introduced between the object and the objective lens.

Conveniently, the number of the multiple areas exceeds nine.

Conveniently, the multiple illuminating light beams scan along scan lines that are arranged in an interlaced manner.

Conveniently, the first beam splitter includes at least one Damman grating.

Conveniently, the first scanner is an acousto-optic device.

Conveniently, adjacent illuminating light beams scan partially overlapping areas of the object.

Conveniently, an illuminating light beam forms a spot on the object, wherein the spot exceeds few tenths of pixels.

A method for inspecting a object, the method includes: generating, by a traveling lens acousto-optic device, a traveling lens that propagates through an active region of the traveling lens acousto-optic device; directing, by a first scanner, a beam of light towards the traveling lens while the traveling lens propagates; splitting, by a first beam splitter, a beam formed by the traveling lens to provide multiple scanning illuminating light beams; directing the multiple illuminating light beams towards multiple areas of the object; and directing multiple reflected light beams from the multiple areas towards multiple detectors; wherein each detector is associated with an area of the multiple areas.

Conveniently, the stage of directing, by a first scanner, the beam of light includes directing the beam of light towards the traveling lens such that most of the beam of light impinges on the traveling lens.

Conveniently, the stage of directing, by a first scanner, the beam of light includes scanning the traveling lens acousto-optic device during a short scanning period that is shorter than one micro-second.

Conveniently, the method includes scanning multiple scan lines by the multiple illuminating light beams along a scan direction that is traverse to a direction of a mechanical movement introduced between the object and the objective lens.

Conveniently, the stage of directing the multiple illuminating light beams towards multiple areas of the object includes directing the multiple beams towards at least nine areas.

Conveniently, the method includes scanning multiple scan lines by the multiple illuminating light beams wherein the multiple scan lines are arranged in an interlaced manner.

Conveniently, the stage of splitting, by a first beam splitter, includes splitting by at least one Damman grating.

Conveniently, the stage of directing, by a first scanner, a beam of light includes directing, by an acousto-optic device, the beam of light.

Conveniently, the method includes mechanically moving the object along a mechanical movement direction.

Conveniently, the stage of directing the multiple illuminating light beams towards multiple areas of the object includes illuminating the object by multiple spots; wherein each spot exceeds few tenths of pixels.

DETAILED DESCRIPTION OF THE INVENTION

The following detailed description is of exemplary embodiments of the invention but the invention is not limited thereto, as modifications and supplemental structures may be added, as would be apparent to those skilled in the art. In particular, but without limitation, while an exemplary embodiment may be disclosed with regard to the inspection of a subject surface by detecting reflected light using a light source and detecting unit that are disposed on a common side of a object (a "reflective system"), it would be readily apparent to one skilled in the art that the teachings are readily adaptable to the inspection of a object by detecting transmitted light with a detecting unit that is on a side of a object opposite to that of the light source (a "transmissive system"). While the reflective system and the transmissive system differ, for one example by the absence of a beam splitter in the transmissive system, the principles of the present invention are applicable to both types of systems. As would be understood by one skilled in the art, both types of systems may be utilized separately or together in the inspection of an object, in accordance with the present invention.

The present invention involves a system for inspecting an object using a single light source that provides a beam of light. The beam of light scans an active region of a traveling lens acousto-optic device in synchronization with a propagation of a traveling lens within that active region.

The traveling lens is generated by providing a radio frequency (RF) chirp. Conveniently, most of the energy of the light beam is directed onto the traveling lens. The traveling lens acousto-optic device generates a traveling spot beam. The spot beam is split, by a beam splitter (such as but not limited to a Damman grating), to multiple light beams that illuminate multiple areas of a surface of an inspected object.

The system also includes a collection path that collects light reflected an/or scattered from the multiple illuminated area and directs the collected light beams to an array of light detectors, wherein different light detector detects light from different illuminated areas.

Figure 1:
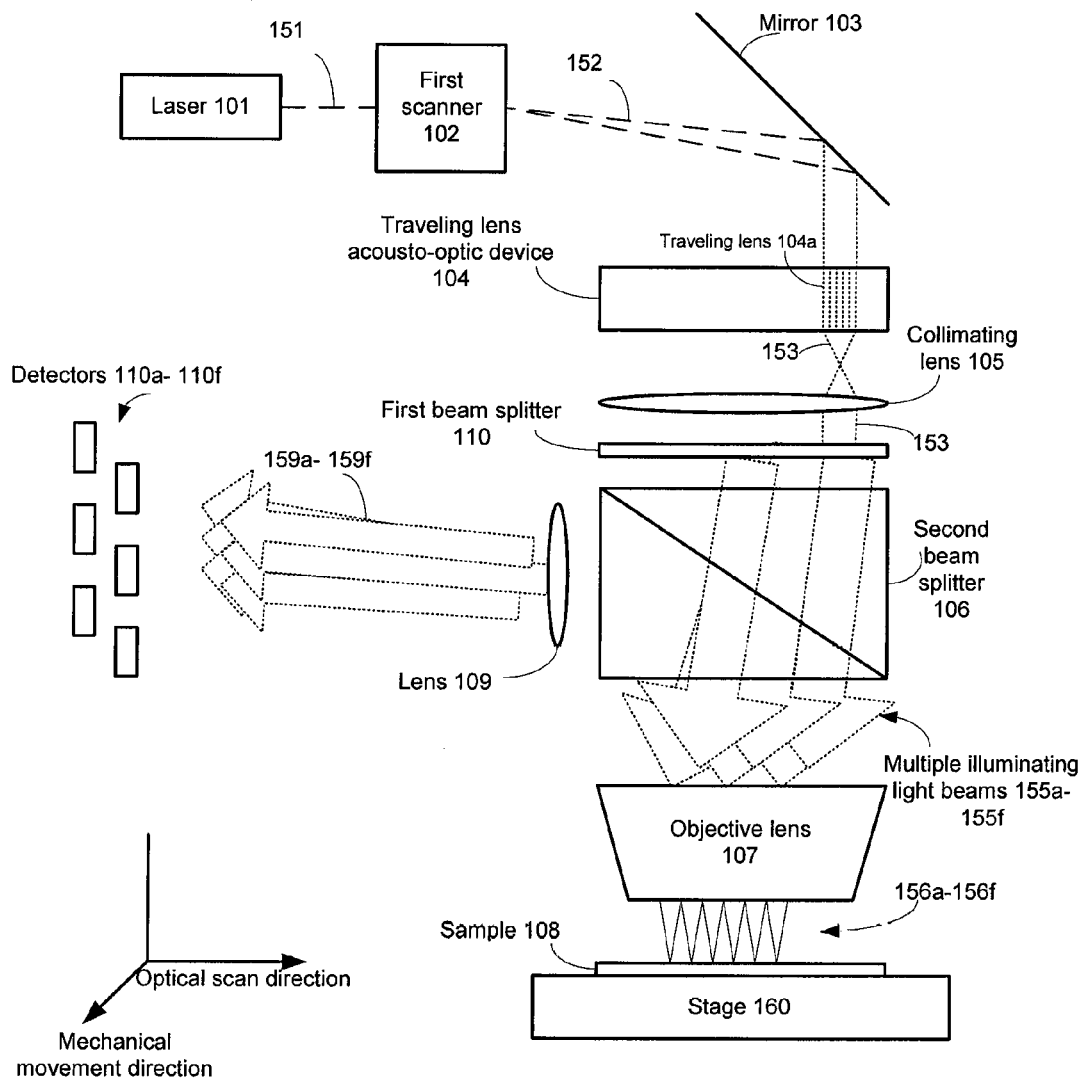
FIG. 1 illustrates a schematic representation of a first exemplary samples and of a sample inspection system according to an embodiment of the invention.

FIG. 1 is a schematic illustration of an object 108 and object inspection system 100 according to an embodiment of the invention.

Without limitation and only by example, the object may be any semiconductor product, such as 8 inch or 12 inch wafers or the like having multiple semiconductor devices thereon, at any of several stages of manufacture, or may be a mask, reticle or the like used in a manufacturing process, where such object must be inspected for defects, foreign objects or pattern accuracy. It is desirable in such systems to identify with high accuracy and reliability the size, location and type of structure, defect or object that appears on the object surface. It also is desirable to undertake such identification at high speed, in order to minimize the delay in the manufacturing process that is provided to the inspection and quality assurance steps.

The system 100 relies upon a light source, such as a CW (or pulse) laser 101 that produces beam of light 151. Beam of light 151 is applied to a first scanner 102 that can deflect the beam of light towards mirror 103, such as to scan a traveling lens acousto-optic device 104 in synchronization with a propagation of traveling lens 104a formed within an active region of the traveling lens acousto-optic device.

It is noted that mirror 103 can be placed between laser 101 and first scanner 102, between traveling lens acousto-optic device 104 and first collimating lens 105 and even be absent from system 10.

The light of beam is directed towards the traveling lens and conveniently most of the beam of light impinges on the traveling lens. A portion of the beam of light that is directed outside the traveling lens will not illuminate the sample, thus by directing most is not all of the beam of light onto the traveling lens, the efficiency of the illumination process is increased.

It is noted that the term light refers to electromagnetic radiation at the visible range as well as ultraviolet, deep ultra violet and extreme deep ultra violet radiation. For wafer inspection, the laser preferably operates at a short wavelength, for example, 248 nm or 193 nm, in order to produce high resolution, with stable output power (or stable pulse energy and pulse rate), a stable transverse mode and a stable beam pointing.

At a given point in time a single traveling lens exists within the traveling lens acousto-optic device 104. Once a traveling lens ends to propagate through the active region of traveling lens acousto-optic device 104 a new traveling lens is formed and first scanner 102 starts a new scan process.

Device 10 can synchronize between the propagation of the traveling lens and the scanning of the beam of light 153 in various manners. For example a controller can control both operations, and one device can synchronize itself to the other.

The traveling lens acousto-optic device 104 is responsive to each of a series of chirped RF pulses, a single pulse resulting in the generation of a single lens and the series of pulses resulting in the formation of multiple cascaded lenses in the traveling lens device 104. Each lens will receive and focus the input laser light at its output, thereby forming the desired number of beams. As the RF pulses migrate through the device 104, the associated lenses will travel, causing each of their beams to move in the nature of a scan.

The basic theory, structure and material of the acousto-optic cell is taught in "Optical Scanning", edited by Gerald F. Marshall, Chapter 11 (published by Marcel Dekker, Inc. in 1991). As explained at pages 675-677, frequency chirp scanning of a single beam involves an acousto-optic Bragg cell to which a linear frequency sweep (the "chirp") is applied. A frequency gradient produced across the optical aperture of the cell will act as a cylindrical lens whose focal length is based on the chirp rate. The light diffracted by the linearly swept acoustic frequency may be converging or diverging, and may be compensated by complementary optical lenses. In accordance with that disclosure, acousto-optic scanners provide significant advantages in cost and performance, particularly where random access times are short. The acousto-optic scanner typically generates one scanning beam, and where multiple beams are desired, as disclosed at pages 682-83 of Marshall's book, multiple chirp cells are required, each receiving chirped RF pulses. Specifically, when a linear increasing frequency is applied to the driver of each of a plurality of chirp cells in an array, a phase grating with pitch increasing in the time domain is set up as a continuous angle scan of each collimated beam of the array is produced according to the Bragg condition, thereby yielding a linear scan of the array of spots. At high frequency cutoff, the driver signal is set to zero, thereby allowing for dissipation of the acoustic energy in the chirp cells and resetting the spots before initiation of the next scan.

Two types of acoustic array scanners are taught in Marshall at pages 682-683, including one where bandwidth is multiplied and another where resolution is multiplied. In the first case, a large number of individually-driven, small and closely arranged transducers are mounted in parallel on an acousto-optic medium made from $TeO_2$ glasses and from $PbMoO_4$ and $TeO_4$ crystals. The second case of acousto-optic array involves an arrangement of the elements in series. The array of scanners, each with a particular resolution (points per line) can yield a greater resolution (points per line) by using complex optics.

By contrast, the acousto-optic device 104 that is used in the present invention employs a single crystal that is effective to generate a single traveling lens in response to an RF chirp. The single crystal in the device is composed of a material that is compatible with a UV light source, preferably having an acousto-optic medium made of fused silica, GaAs or $TeO_2$ glass, although other known materials having Ultra Violet light compatibility, may be used. The crystal has an anti-reflective coating on each major side that rated at less than 0.5% for both sides. The device will operate in a longitudinal acoustic mode at a wavelength of 266 nm and at a center frequency of 200 MHz with a bandwidth of 130 MHz. RF power is less than 3.0 watts. The active aperture of the device may be 1.0 mm "H" by 60 mm "L" in one exemplary embodiment.

The traveling lens acousto-optic device 104 can resemble the traveling lens of acousto-optic device illustrated in U.S. Pat. Nos. 6,809,808, 7,053,395, 6,943,898, 6,853,475 and 7,002,695 all being incorporated herein by reference.

Traveling lens acousto-optic device 104 outputs a beam (also referred to as spot beam) 153 that passes through collimating lens 105 to be directed towards first beam splitter 110.

The first beam splitter 153 can include one or more Damman gratings. First beam splitter 153 can include one or more one-dimensional or two-dimensional Damman gratings.

Figure 2:
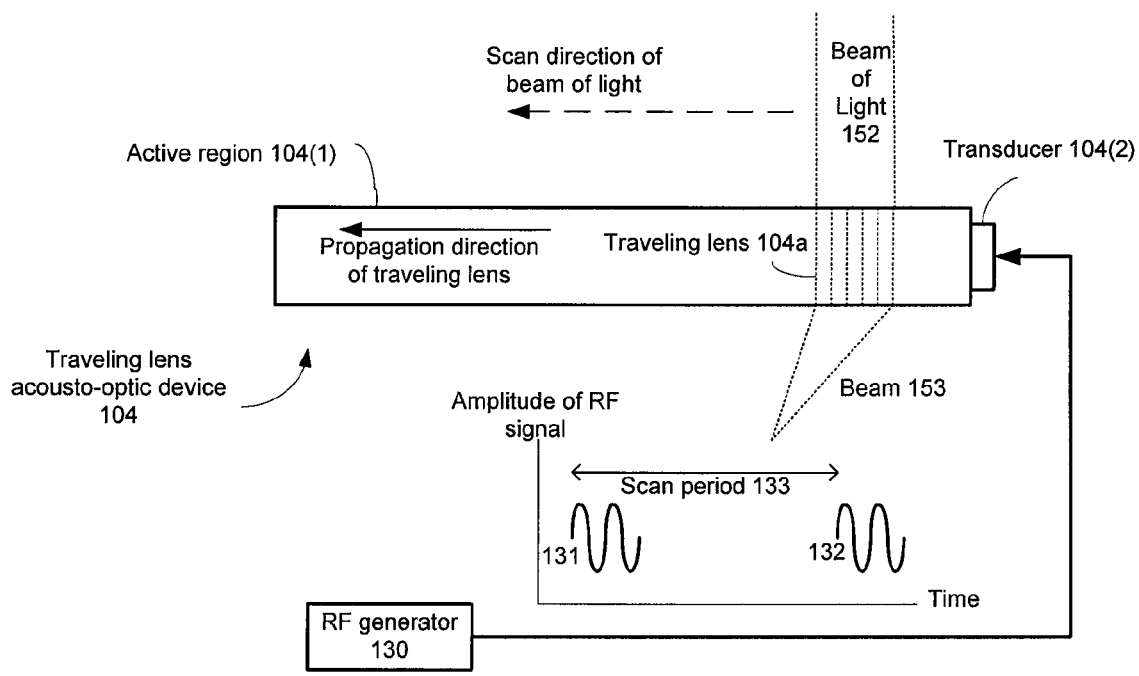
FIG. 2 illustrates a traveling lens acousto-optic device and a radio frequency generator according to an embodiment of the invention.

The beam splitter 153 splits the beam to multiple illuminating light beams 155a-155f. It is noted that although six illuminating light beams are illustrated in FIG. 2 that the number of illuminating light beams can differ from six. For example, the number of illuminating light beams can exceed nine.

The one or more Damman grating can be designed and positioned to provide multiple splitting patterns. The design and placing of Damman gratings is known in the art are requires no additional explanation.

Multiple illuminating light beams 155a-155f. are incident onto second beam splitter 106 that passes these beams onto objective lens 107 that directs these light beams (illustrated as 156a-156f) onto multiple areas of sample 108. Conveniently, illuminating beams 156a-156f are parallel to each other and their optical axes are perpendicular to sample 108.

Light reflected or scattered from the multiple samples are collected by a collection path that includes objective lens 107, second beam splitter 106, and second collimating lens 109. The collection path directs each collected light beam 159a-159f towards a detector (out of detectors 110a-110f) that is associated with a single area.

For simplicity of explanation the light beams that pass through objective lens 107 towards second beam splitter and from second beam splitter 106 towards second collimating lens 109 are not shown.

Detectors 110a-110f detect light from the multiple illuminated areas of sample 108. They generate detection signals that can be stored and later on processed in order to detect defects. Detect detection methods such as die to die comparison, die to golden die comparison, die to design rule comparison are known in the art and require no additional explanation.

The inventors used non-imaging detectors but this is not necessarily so imaging detectors can be used, especially when the collection path is designed such as to image the illuminated areas of sample 108 onto the detectors.

It is noted that a CCD array or another detector array can be regarded as multiple detectors.

It is noted that although FIG. 1 illustrates bright field illumination and collection that system 100 can apply dark field illumination and collection as well as a combination of dark field and bright field techniques, as illustrated in U.S. Pat. No. 6,853,475 of Feldman et al., which is incorporated herein by reference.

System 100 also include stage 160 that supports and moves sample 108 along a mechanical movement direction that is traverse (and even perpendicular) to a scan direction of the multiple illuminating light beams 156a-156f.

It is noted that system 100 can also move various optics such as objective lens 170 while maintaining sample 108 at the same position. Alternatively, both optics and sample can be mechanically transferred.

Yet according to an embodiment of the invention the sample 108 is rotated by stage 160 (for example—it is rotated about its axis).

FIG. 2 illustrates traveling lens acousto-optic device 104 and radio frequency (RF) generator 130 according to an embodiment of the invention.

Beam of light 152 is directed onto traveling lens 104a that propagates within active region 104(1) of traveling lens acousto-optic device 104. Traveling lens 104a is generated in response to an RF chirp that is provided by RF generator 130. These RF chirps are provided to a transducer 104(2) that is positioned to be transverse to the path of the beam of light and enables the RF waveforms to be injected at the edge of the active region 104(1) of a crystal and to establish a pressure wave that traverses the length of the crystal at a velocity that, in an exemplary embodiment, is 5.96 milimeter per microSecond or approximately the speed of sound. The pressure waves that propagate through the crystal medium are aligned to provide focusing lens 104a. Beam of light 152 passes through traveling lens 104a to form beam 153 that is focused at a focal point.

Figure 3:
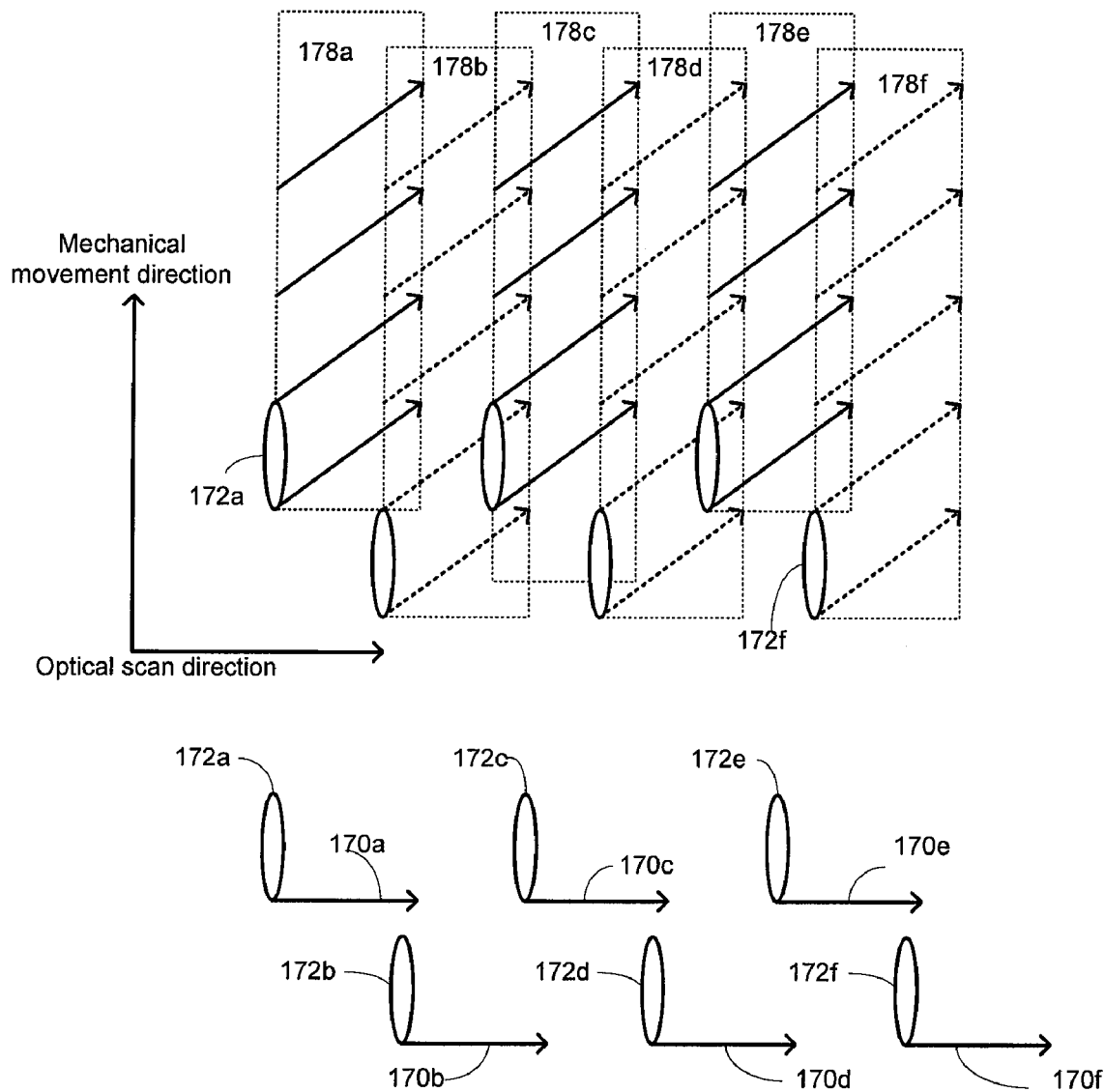
FIG. 3 is a schematic illustration of an illumination patterns and scan lines according to an embodiment of the invention.

FIG. 3 is a schematic illustration of an illumination pattern and scan lines according to an embodiment of the invention.

FIG. 3 illustrates the relationship between optical scan lines, mechanical movement of the sample and the actual scanning pattern that is achieved by a combination of optical scanning a mechanical movement.

Beam of light 152 scans traveling lens acousto-optic device (and traveling lens 104a propagates along a parallel propagation axis) causing each of multiple illuminating beams 156a-156f to perform a scan along scan lines 170a-170f. Each illuminating light beam is illustrated as a spot (172a-172f) on sample 108. These scan lines are parallel to each other and are illustrated in FIG. 3 as arranged in an interlaced manner. It is noted that the x-axis projections of these scan lines partially overlap.

Sample 108 is mechanically transferred along a mechanical movement direction that is traverse (can be perpendicular) to scan lines 170a-170f.

The combination of both optical scan and mechanical movement result in an angled scanning pattern that is angled up to the right because of the upward mechanical movement of the sample 108.

Due to the partial overlap of the x-axis projections of adjacent scan lines the area that is scanned by adjacent illuminating light beams partially overlap, as illustrated by the overlap between areas 178a-178f.

Figure 4:
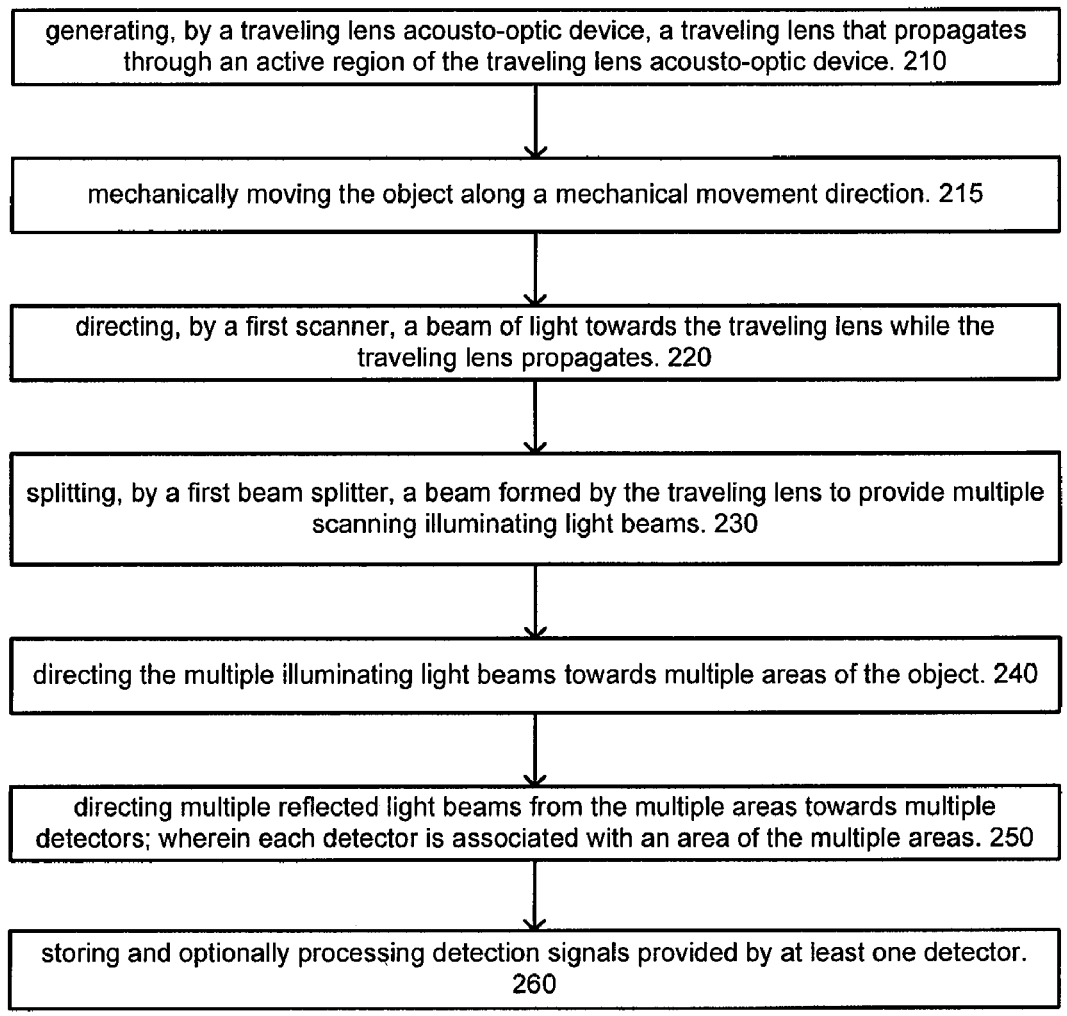
FIG. 4 is a flow chart illustrating a method for inspecting an object according to an embodiment of the present invention.

FIG. 4 is a flow chart illustrating method 200 for inspecting an object according to an embodiment of the present invention.

It is noted that various stages of method 200 at least partially overlap and that their order as illustrated in FIG. 4 is not mandatory.

Method 200 starts by stages 210 and 215. Stage 210 includes generating, by a traveling lens acousto-optic device, a traveling lens that propagates through an active region of the traveling lens acousto-optic device.

Stage 215 includes stage 215 of mechanically moving the object along a mechanical movement direction.

Stage 210 is followed by stage 220 of directing, by a first scanner, a beam of light towards the traveling lens while the traveling lens propagates. The product of stage 220 is a light beam that propagates along with the propagation of the traveling lens.

Conveniently, stage 220 includes directing, by an acousto-optic device, the beam of light.

Stage 220 is followed by stage 230 of splitting, by a first beam splitter, a beam formed by the traveling lens to provide multiple scanning illuminating light beams.

Conveniently, stage 230 includes splitting by a two dimensional Damman grating.

Stage 230 is followed by stage 240 of directing the multiple illuminating light beams towards multiple areas of the object.

Conveniently, stage 240 includes scanning multiple scan lines by the multiple illuminating light beams along a scan direction that is traverse to a direction of a mechanical movement introduced between the object and the objective lens.

Conveniently, stage 240 includes directing the multiple beams towards at least nine areas.

Conveniently, stage 240 includes scanning multiple scan lines by the multiple illuminating light beams wherein the multiple scan lines are arranged in an interlaced manner.

Stage 240 is followed by stage 250 of directing multiple reflected light beams from the multiple areas towards multiple detectors; wherein each detector is associated with an area of the multiple areas.

Stage 250 is followed by stage 260 of storing and optionally processing detection signals provided by at least one detector.

According to another embodiment of the invention fewer detectors are used and instead of using multiple detectors per scan line (such as detectors 110a, 110c and 110e) a single detector should per scan line but the scan line should be longer than the scan line illustrated in FIG. 3. In such a case multiple sensors can be positioned one under the other and the scanning lines should be arranged in an interlacing manner.

While the present invention has been described with respect to certain exemplary embodiments, it is not limited thereto, and the full scope of the present invention is defined in the appended claims, as interpreted in accordance with applicable law.

We claim:
1. A system for inspecting a object, the system comprises:
   a traveling lens acousto-optic device adapted to generate a traveling lens that propagates through an active region of the traveling lens acousto-optic device;
   a first scanner, adapted to scan a beam of light across and in synchronization with the traveling lens while the traveling lens is propagating through the active region of the traveling lens acousto-optic device;
   a first beam splitter, adapted to receive a beam formed by the traveling lens; and to split the scanned beam to multiple illuminating light beams;
   multiple detectors;
   an objective lens; adapted to receive the multiple illuminating light beams, direct the multiple illuminating light beam towards multiple areas of the object, receive multiple collected light beams from the multiple areas of the object, and direct the multiple collected light beams towards the multiple detectors;
   wherein each detector is associated with an area of the multiple areas.

2. The system according to claim 1 wherein the first scanner is adapted to direct the beam of light towards the traveling lens so as to cause most of the beam of light to impinge on the traveling lens.

3. The system according to claim 1 wherein the beam of light scans the traveling lens acousto-optic device during a short scanning period that is shorter than one micro-second.

4. The system accordingly to claim 1 adapted to scan the multiple illuminating light beams, along a scan direction that is traverse to a direction of a mechanical movement introduced between the object and the objective lens.

5. The system according to claim 1 wherein the number of the multiple areas exceeds nine.

6. The system according to claim 1 wherein the multiple illuminating light beams scan along scan lines that are arranged in an interlaced manner.

7. The system according to claim 1 wherein the first beam splitter comprises at least one Damman grating.

8. The system according to claim 1 wherein the first scanner is an acousto-optic device.

9. The system according to claim 1 wherein adjacent illuminating light beams scan partially overlapping areas of the object.

10. The system according to claim 1 wherein an illuminating light beam forms a spot on the object, wherein the spot exceeds few tenths of pixels.

11. A method for inspecting a object, the method comprises:
- generating, by a traveling lens acousto-optic device, a traveling lens that propagates through an active region of the traveling lens acousto-optic device;
- scanning, by a first scanner, a beam of light across and in synchronization with the traveling lens while the traveling lens is propagating through the active region of the traveling lens acousto-optic device;
- splitting, by a first beam splitter, a beam formed by the traveling lens to provide multiple scanning illuminating light beams;
- directing the multiple illuminating light beams towards multiple areas of the object; and
- directing multiple reflected light beams from the multiple areas towards multiple detectors; wherein each detector is associated with an area of the multiple areas.

12. The method according to claim 11 wherein scanning, by a first scanner, the beam of light comprises directing the beam of light towards the traveling lens so as to cause most of the beam of light to impinge on the traveling lens.

13. The method according to claim 11 wherein directing, by a first scanner, the beam of light comprises scanning the traveling lens acousto-optic device during a short scanning period that is shorter than one micro-second.

14. The method according to claim 11 wherein the method comprises scanning multiple scan lines by the multiple illuminating light beams along a scan direction that is traverse to a direction of a mechanical movement introduced between the object and the objective lens.

15. The method according to claim 11 wherein directing the multiple illuminating light beams towards multiple areas of the object comprises directing the multiple beams towards at least nine areas.

16. The method according to claim 11 wherein the method comprises scanning multiple scan lines by the multiple illuminating light beams wherein the multiple scan lines are arranged in an interlaced manner.

17. The method according to claim 11 wherein the stage of splitting, by a first beam splitter, comprises splitting by at least one Damman grating.

18. The method according to claim 11 wherein directing, by a first scanner, a beam of light comprises directing, by an acousto-optic device, the beam of light.

19. The method according to claim 11 further comprising mechanically moving the object along a mechanical movement direction.

20. The method according to claim 11 wherein directing the multiple illuminating light beams towards multiple areas of the object comprises illuminating the object by multiple spots; wherein each spot exceeds few tenths of pixels.

* * * * *